(12) United States Patent
Shiozawa et al.

(10) Patent No.: US 10,265,036 B2
(45) Date of Patent: Apr. 23, 2019

(54) RADIOGRAPHIC APPARATUS

(71) Applicant: CANON KABUSHIKI KAISHA, Tokyo (JP)

(72) Inventors: Takashi Shiozawa, Tokyo (JP); Kazuyuki Ueda, Tokyo (JP); Kazuya Tsujino, Tokyo (JP); Nobuhiro Ito, Yamato (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 169 days.

(21) Appl. No.: 15/039,658

(22) PCT Filed: Sep. 11, 2014

(86) PCT No.: PCT/JP2014/074757
§ 371 (c)(1),
(2) Date: May 26, 2016

(87) PCT Pub. No.: WO2015/079782
PCT Pub. Date: Jun. 4, 2015

(65) Prior Publication Data
US 2017/0027531 A1 Feb. 2, 2017

(30) Foreign Application Priority Data
Nov. 29, 2013 (JP) .................. 2013-247133

(51) Int. Cl.
| A61B 6/00 | (2006.01) |
| A61B 6/02 | (2006.01) |
| A61B 6/04 | (2006.01) |
| A61B 6/10 | (2006.01) |

| H01J 35/06 | (2006.01) |

(Continued)

(52) U.S. Cl.
CPC .............. *A61B 6/107* (2013.01); *A61B 6/025* (2013.01); *A61B 6/0414* (2013.01); *A61B 6/405* (2013.01);
(Continued)

(58) Field of Classification Search
CPC ....... A61B 6/0414; A61B 6/025; A61B 6/107; A61B 6/4007; A61B 6/405; A61B 6/42;
(Continued)

(56) References Cited

U.S. PATENT DOCUMENTS 6,370,218 B1 * 4/2002 Toth ........................ A61B 6/032
378/113
2004/0211909 A1 * 10/2004 Watanabe .............. G03B 42/02
250/370.11

(Continued)

FOREIGN PATENT DOCUMENTS

| JP | S6483139 A | 3/1989 |
| JP | H01204649 A | 8/1989 |

(Continued)

*Primary Examiner* — Chih-Cheng Kao
(74) *Attorney, Agent, or Firm* — Canon USA, Inc., IP Division (57) ABSTRACT

A radiographic apparatus includes a target array and an X-ray detecting unit. The target array includes a plurality of targets and a forward shielding member. The X-ray detecting unit includes a detecting portion. The X-ray detecting unit further includes a shielding portion extending toward an outer side of the detecting portion along an array direction in which the targets are arrayed.

16 Claims, 9 Drawing Sheets

(51) Int. Cl.
*H01J 35/08* (2006.01)
*H01J 35/16* (2006.01)

(52) U.S. Cl.
CPC .............. *A61B 6/4007* (2013.01); *A61B 6/42* (2013.01); *A61B 6/502* (2013.01); *H01J 35/06* (2013.01); *H01J 35/08* (2013.01); *H01J 35/16* (2013.01); *H01J 2235/068* (2013.01); *H01J 2235/087* (2013.01)

(58) Field of Classification Search
CPC ................ A61B 6/502; H01J 2235/068; H01J 2235/087; H01J 35/06; H01J 35/08; H01J 35/16
See application file for complete search history.

(56) References Cited

U.S. PATENT DOCUMENTS

| | | | |
|---|---|---|---|
| 2009/0232270 A1* | 9/2009 | Okunuki | A61B 6/00 378/5 |
| 2010/0119033 A1* | 5/2010 | Li | A61B 6/06 378/5 |

FOREIGN PATENT DOCUMENTS

| | | |
|---|---|---|
| JP | 2001037746 A | 2/2001 |
| JP | 2009205992 A | 9/2009 |
| JP | 2012120651 A | 6/2012 |

* cited by examiner

RADIOGRAPHIC APPARATUS

TECHNICAL FIELD

The present invention relates to a radiographic apparatus used in the field of medical equipment. In particular, the present invention relates to a radiographic apparatus including an X-ray generating unit, the X-ray generating unit including a plurality of targets and a forward shielding member.

BACKGROUND ART

In the field of recent radiography such as mammography, tomosynthesis imaging has come to be employed as a method of separating information on an object in the depth direction of the object. In tomosynthesis imaging, a plurality of images are acquired by applying X-rays to an object from a plurality of angles, and the plurality of images thus acquired are reconstructed into a tomographic image.

Japanese Patent Laid-Open No. 2003-325499 discloses a mammotomographic apparatus including a mechanical structure that rotates an X-ray generating tube. Japanese Patent Laid-Open No. 2003-325499 further discloses a method in which a tomographic image of a breast is acquired by exposing the breast with X-rays while changing the angle of exposure within a predetermined range.

However, such a mammotomographic apparatus including a rotating mechanism has a problem in that the acquired image may be blurred because of the rotational movement of the X-ray generating tube during imaging. Such a blur in the acquired image may produce an artifact in a tomographic image obtained by the reconstruction of images. Moreover, noise generated by the movement of the X-ray generating tube sometimes makes the examinee feel nervous during imaging.

Accordingly, a tomosynthesis imaging technique has been proposed in which X-rays are applied to an object from a plurality of angles by sequentially using a plurality of X-ray sources that are held stationary. On the other hand, United States Patent Application Publication No. 2004/0213378 discloses a radiographic apparatus that includes an X-ray source unit in which a plurality of X-ray sources are arrayed at predetermined intervals, and a shielding member unit having a plurality of apertures provided in correspondence with the X-ray sources that are arrayed.

SUMMARY OF INVENTION

Technical Problem

One of major factors that determine the resolution of an image acquired by a radiographic apparatus is the focal spot diameter of the X-ray source. In each embodiment of the present invention, the size of focal spots of the radiographic apparatus substantially corresponds to the size of focal spots of electron beams emitted from electron emitting sources to the respective targets. Hereinafter, the focal spot of an electron beam that is defined on a target is referred to as "focal spot."

From the viewpoint of increasing the resolution of an image to be acquired, the focal spot diameter is desired to be as small as possible. On the other hand, from the viewpoints of the heat resistance of a material forming the target and the intensity of the X-rays, the lower limit and the upper limit are set forth for each of the density of the anode current flowing through the target and the focal spot diameter. In general, a finite "focal spot diameter" is employed with a lower limit of several dozens of microns in view of heat resistance of the target and with an upper limit of several millimeters in view of resolution.

In the radiographic apparatus disclosed by United States Patent Application Publication No. 2004/0213378, the shielding member unit having the plurality of apertures that are provided in correspondence with the array of X-ray sources included in the X-ray source unit is provided on the front side of the X-ray source unit.

The shielding member unit includes "partitions" so that the plurality of X-ray beams can be extracted separately from one another in a predetermined direction. The partitions have a "height (thickness)" for attenuating the X-rays so as to prevent the emission of X-rays in undesired directions. In general, the "height" of the partitions included in the shielding member unit ranges from 0.1 mm or larger to several dozens of millimeters or smaller in a direction from the focal spots toward an X-ray detecting unit.

In the radiographic apparatus including such a shielding member unit, penumbras attributed to the "focal spot diameter" and the "height" of the partitions of the shielding member unit are inevitably formed on the outer sides of the X-ray beam along a direction in which the plurality of targets are arrayed. A penumbra is an imperfect X-ray beam whose focal image seen from a detector is partially eclipsed. The penumbra is an unnecessary component that may causes an artifact in the acquired image. Moreover, the intensity of X-rays forming the penumbra varies in the direction in which the plurality of targets are arrayed. Therefore, the penumbra is an unnecessary component also in terms of triggering deterioration in the quality of the acquired image.

In a radiographic apparatus including a single target, penumbras can be reduced to an ignorable level by increasing the "height" of a forward shielding member. On the other hand, in a radiographic apparatus including a plurality of targets and a shielding member unit, a plurality of X-ray beams are made to coincide with one another. To do so, the "height" of the partitions is limited. Consequently, large penumbra regions are produced.

Moreover, since such penumbras are produced on the outer sides of a main exposed region, whose focal spot is not eclipsed, in the direction in which the plurality of targets are arrayed, the penumbras tend to leak to the outside of the radiographic apparatus rather than into the main exposed region.

To suppress the leakage of penumbras to the outside of the radiographic apparatus, the entirety of the radiographic apparatus may be covered with a shielding member. In such a configuration, however, the weight increases and the center of gravity is raised. Consequently, the radiographic apparatus becomes unstable, increasing the probability of image blurring during imaging. Hence, in terms of usability and imaging performance, there has been a demand for a radiographic apparatus in which the range of the penumbra is limited by an effective arrangement of shielding members.

The present invention provides a radiographic apparatus in which the penumbra that may leak to the outside of the radiographic apparatus is effectively reduced.

Solution to Problem

According to an aspect of the present invention, there is provided a radiographic apparatus including an X-ray generating unit that includes a target array including a plurality of targets that are arrayed in a line and a forward shielding member, the forward shielding member including a plurality of partitions that each separate adjacent ones of the targets, and an electron emitting source that emits electron beams to electron incident surfaces of the plurality of targets, respectively; and an X-ray detecting unit that includes a detecting portion facing the target array and including a plurality of detecting devices, and a shielding portion provided on an outer side of the detecting portion along an array direction in which the targets are arrayed in a line. The X-ray generating unit forms a main exposed area and a penumbra area on the X-ray detecting unit, the penumbra area being formed on the outer side of the main exposed area. The shielding portion includes at least a part positioned in the penumbra area.

Further features of the present invention will become apparent from the following description of exemplary embodiments with reference to the attached drawings.

DESCRIPTION OF EMBODIMENTS

Embodiments of the present invention concerning an X-ray generating unit and a mammotomographic apparatus will now be described with reference to the attached drawings. The materials, dimensions, shapes, relative positions, and other factors of elements described in the following embodiments do not limit the scope of the present invention unless otherwise stated.

A radiographic apparatus according to a general embodiment of the present invention will first be described with reference to FIGS. 1A to 6.

Figure 1A:
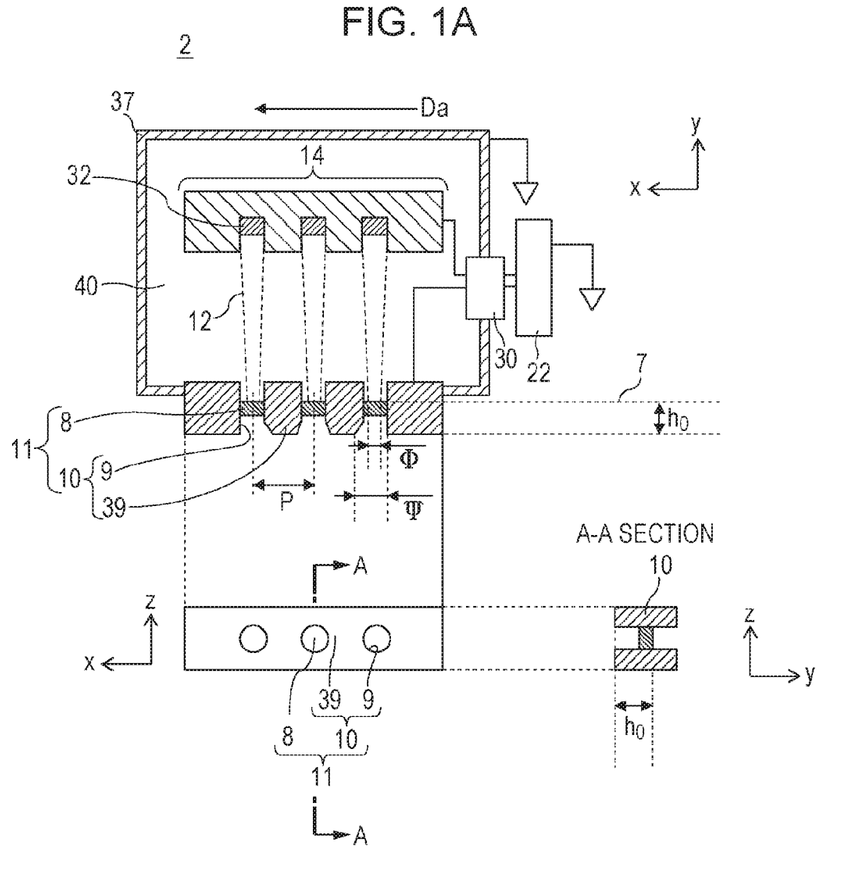
FIG. 1A is a three-way view of an X-ray generating unit according to a general embodiment of the present invention.
Figure 1B:
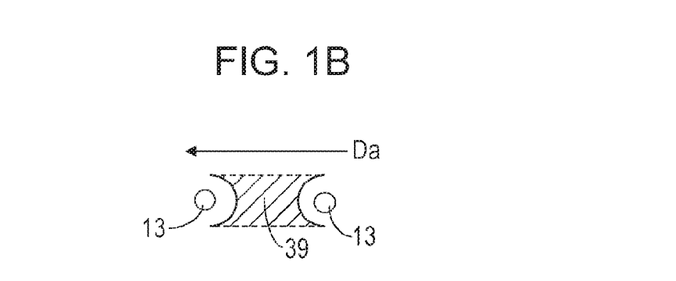
FIG. 1B is an enlarged view illustrating part of a partition.

An X-ray generating unit 2 included in a radiographic apparatus 1 according to the general embodiment of the present invention will be described with reference to FIGS. 1A, 1B, 2A, and 2B. FIG. 1A is a three-way view of the X-ray generating unit 2 according to the general embodiment of the present invention. FIG. 1B is an enlarged view illustrating one of partitions 39 included in a forward shielding member 10.

As illustrated in FIG. 1A, the X-ray generating unit 2 according to the general embodiment includes a target array 11 and an electron emitting source 14. The target array 11 includes a plurality of targets 8 that generate X-rays, and the forward shielding member 10. The electron emitting source 14 includes a plurality of electron emitting portions 32.

As illustrated in FIGS. 1A and 1B, the plurality of targets 8 are each a transmission-type target having an electron incident surface 7 and an emitting surface that is opposite the electron incident surface 7. The targets 8 are arrayed in a line in a predetermined array direction Da.

As illustrated in FIGS. 1A and 1B, the forward shielding member 10 has a plurality of apertures 9 provided in correspondence with the plurality of targets 8. That is, the plurality of apertures 9 are arrayed along the array direction Da, as with the plurality of targets 8. The forward shielding member 10 further includes a plurality of partitions 39 that each separate adjacent ones of focal spots 13 from each another as illustrated in FIG. 1B. The partitions 39 each extend in a direction from the electron incident surfaces 7 toward the emitting surfaces of the targets 8. Each pair of partitions 39 are regarded as defining the aperture diameter of a corresponding one of the apertures 9 along the array direction Da.

As illustrated in FIG. 1A, the electron emitting source 14 is configured such that electron beams 12 are applied to the electron incident surfaces 7 of the plurality of targets 8, respectively, whereby the focal spots 13 are formed. In such a configuration, referring now to FIG. 2B, the X-ray generating unit 2 emits X-rays from the focal spots 13 such that a plurality of X-ray beams 38 that are separate from one another along the array direction Da by the partitions 39 are extracted from the plurality of apertures 9, respectively. In FIG. 2B, the focal spots 13 formed on the respective electron incident surfaces 7 of the targets 8 are not illustrated.

The shapes of the partitions 39 and the apertures 9 along the array direction Da that characterize the X-ray generating unit 2 according to the general embodiment of the present invention will now be described with reference to FIGS. 2A and 2B.

Figure 2A:
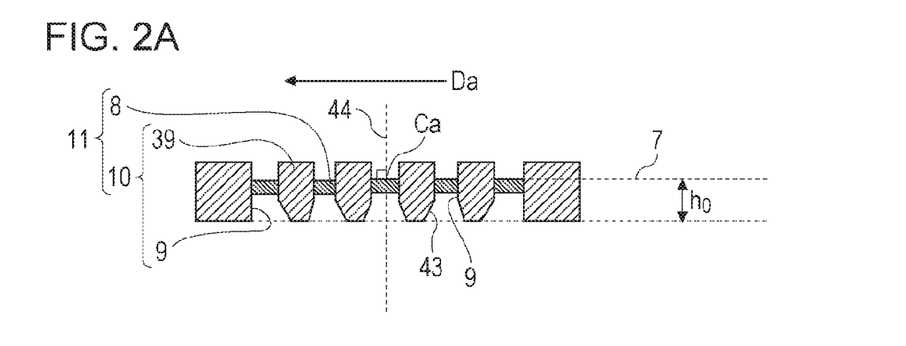
FIG. 2A is an enlarged view illustrating a target array included in the X-ray generating unit according to the general embodiment of the present invention.
Figure 2B:
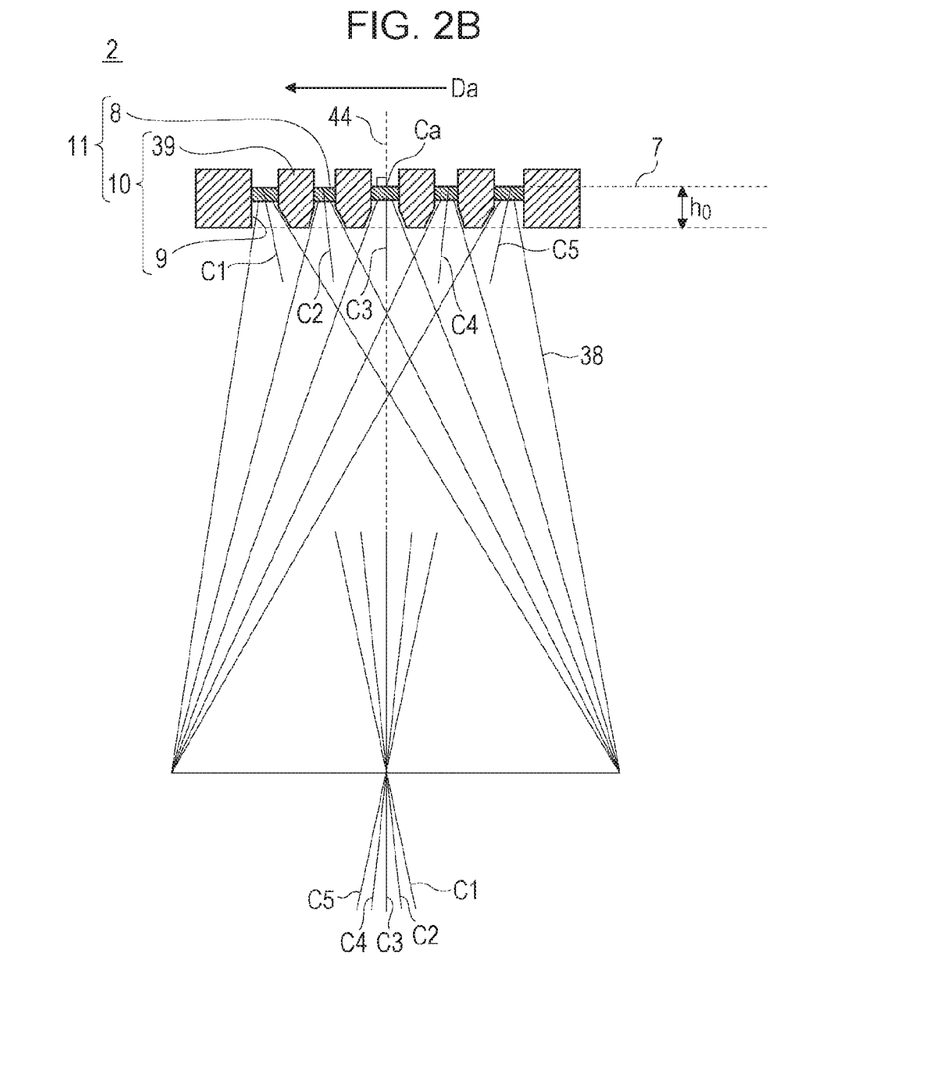
FIG. 2B is an enlarged view illustrating how X-ray beams coincide with one another.

FIG. 2A illustrates an embodiment of the target array 11 in which a number n of targets 8 that are arrayed is five. As illustrated in FIG. 2A, the plurality of partitions 39 each have sloping surfaces 43 that slope with respect to a normal line 44, which is one of lines normal to the electron incident surfaces 7. The normal line 44 passes through an array center Ca of the target array 11. As illustrated in FIG. 2B, in the target array 11 according to the general embodiment, the sloping surfaces 43 of the plurality of partitions 39 define center axes C1 to C5 of the respective apertures 9 along the array direction Da. Conical trapezoids are inscribed in the respective apertures 9, with surfaces of the targets 8 on which the focal spots 13 are defined being the upper surfaces of the respective conical trapezoids. The center axes C1 to C5 are each uniquely defined in a corresponding one of the conical trapezoids as a straight line connecting the center of a corresponding one of the focal spots 13 and the center of a corresponding one of planes extending at a height $h_0$ from a corresponding one of the electron incident surfaces 7.

With the X-ray generating unit 2 according to the general embodiment including at least the plurality of targets 8 and the forward shielding member 10 having the apertures 9 provided in correspondence with the targets 8, the problem of vibrations that may occur with the rotational movement of the known X-ray generating unit is avoided. Hence, the X-ray generating unit 2 according to the general embodiment does not have the problem of image blurring caused by vibrations that may occur in the known X-ray generating unit with the rotational movement of the X-ray generating unit.

In the general embodiment, the target array 11 includes the partitions 39 each having the sloping surfaces 43 that define a corresponding one of the apertures 9. Thus, scattering of X-rays attributed to the partitions 39 of the forward shielding member 10 is reduced. Consequently, undesired exposure to the X-rays around the X-ray generating unit 2 is reduced.

In the target array 11 according to the general embodiment, the center axes C1 to C5 of the respective apertures 9 each incline with respect to the normal line 44. The angles of inclination of the center axes C1 to C5 increase as the distances from the normal line 44 to the respective apertures 9 increase. As illustrated in FIG. 2B, the target array 11 according to the general embodiment can form an exposed area in which the X-ray beams 38 having passed through the respective apertures 9 coincide with one another at a predetermined distance from the target array 11.

According to the general embodiment, in the tomography in which X-ray beams are emitted at different angles with respect to the object, a wide imaging field can be defined on the examinee. In other words, for a given imaging field, the number n of targets 8 arrayed in the target array 11 can be increased while a focal spot pitch p is reduced. Thus, an effect of improving the resolution of the tomographic image in the depth direction is produced.

As illustrated in FIG. 2B, from the viewpoints of providing a satisfactory exposed area and improving the resolution in the depth direction, it is desirable that the sloping surfaces 43 of the partitions 39 slope at different angles such that the center axes C1 to C5 of the respective apertures 9 converge. The angles of the sloping surfaces 43 of the partitions 39 with respect to the normal line 44 can be determined in such a manner as to increase with the distances from the apertures 9 to the normal line 44.

While the general embodiment concerns a case where the sloping surfaces 43 are each a flat surface, the sloping surfaces 43 may each be a curved surface. To reduce the scattering of X-rays, the sloping surfaces 43 are desirably provided as flat surfaces.

The forward shielding member 10 has at least a function of shielding part of the X-rays generated by the targets 8. The forward shielding member 10 may also has a function of holding the plurality of targets 8, and a function as an electrode that defines the anode potential of the plurality of targets 8, as in the general embodiment.

The targets 8 are each a transmission-type target having the electron incident surface 7 and the emitting surface that is opposite the electron incident surface 7 and from which X-rays are emitted. As illustrated in FIGS. 1A and 1B, the transmission-type targets 8 separate incident paths along which the electron beams 12 are incident on the targets 8 from extraction paths along which the X-ray beams 38 are extracted from the targets 8. In the general embodiment, the forward shielding member 10 encloses the targets 8 and is connected to the targets 8 in such a manner as to avoid the above paths.

The target array 11 according to the general embodiment including the transmission-type targets 8 and the forward shielding member 10 is superior to that including reflection-type targets in reducing crosstalk that may occur along the array direction Da. Such crosstalk includes at least one of backscattered electrons, backscattered X-rays, and X-rays emitted frontward.

In the case of the transmission-type targets 8, a shielding member can be positioned near the targets 8. In this respect also, the transmission-type targets 8 are superior to the reflection-type targets in terms of reducing the weight and volume of the shielding member and reducing the size of the X-ray generating unit.

While the electron emitting source 14 according to the general embodiment is provided as a cathode array in which the plurality of electron emitting portions 32 are arrayed in correspondence with the respective targets 8, modifications of the electron emitting source 14 are also within the scope of the present invention. For example, the electron emitting source 14 may include at least one electron emitting portion 32 provided with a deflection electrode. In such a modification, the electron beam 12 emitted from the single electron emitting portion 32 can be scanningly moved along the array direction Da of the target array 11. Therefore, the number of electron emitting portions 32 can be made smaller than the number n of targets 8.

In the general embodiment, the electron emitting source 14 is housed in an envelope 37 whose internal space 40 is vacuumed, and the target array 11 is connected to the envelope 37 at an opening of the envelope 37 such that the electron incident surfaces 7 face toward the internal space 40. In the general embodiment, the target array 11 also serves as one of structural members constituting the envelope 37, and the targets 8 are also regarded as windows from which the X-rays are emitted.

The electron emitting portions 32 and the electron incident surfaces 7 are in contact with the internal space 40 of the envelope 37. Therefore, scattering of the electron beams 12 emitted from the electron emitting portions 32 is reduced, whereby the electron beams 12 are assuredly incident on the respective electron incident surfaces 7. Hence, the electron emitting source 14 or the target array 11 may not necessarily be housed in the envelope 37, and part of the electron emitting source 14 or the target array 11 may be exposed to the outside of the envelope 37. The degree of vacuum of the internal space 40 can be set within $10^{-8}$ Pa or higher and $10^{-4}$ Pa or lower for stable emission of electrons.

The envelope 37 can be made of a material having fastness so as to be resistant to atmospheric pressure and also having air-tightness so as to maintain the vacuum. Specifically, the envelope 37 can be made of brass, stainless steel, aluminum, copper, or the like. As illustrated in FIG. 1A, the envelope 37 according to the general embodiment is provided with a current introducing terminal 30 that electrically connects the electron emitting source 14 and a driving circuit 22 to each other. The current introducing terminal 30 may electrically connect the target array 11 and the driving circuit 22 to each other as illustrated in FIG. 1A, or may electrically connect the target array 11 and a ground terminal (not illustrated) to each other.

First Exemplary Embodiment

A radiographic apparatus 1 according to a first exemplary embodiment of the present invention will now be described with reference to FIG. 3. In the first exemplary embodiment, the radiographic apparatus 1 includes at least the X-ray generating unit 2, an X-ray detecting unit 3, and an object positioning portion 4. The X-ray detecting unit 3 faces toward the target array 11. The object positioning portion 4 is provided between the X-ray generating unit 2 and the X-ray detecting unit 3 and on the X-ray detecting unit 3.

The object positioning portion 4 is a space in which an object 25 can be positioned. The object 25 may be a part of a human body such as a breast, a limb, or the head of a examinee; a living thing; an organism for biopsy; and so forth. If the object 25 is a breast, the object positioning portion 4 and the radiographic apparatus 1 function as a breast inserting portion 5 and a mammotomographic apparatus, respectively.

The X-ray detecting unit 3 includes at least a detecting portion 15 and shielding portions 16. A plurality of detecting devices (not illustrated) are provided in the detecting portion 15. The plurality of detecting devices are arrayed two-dimensionally in the detecting portion 15, whereby a two-dimensional image is acquired.

The shielding portions 16 are provided on the respective outer sides of the detecting portion 15 along the array direction Da and each include at least a member that shields an examinee or an operator from X-rays.

The technical significance of the shielding portions 16 will now be described.

The X-ray generating unit 2 including the forward shielding member 10 generates, on a side thereof on which the X-ray detecting unit 3 and the forward shielding member 10 face each other, main exposed regions 38 each having a focal spot that is not eclipsed and penumbra regions 33 each having a focal spot that is partially eclipsed. The main exposed regions 38 are each accompanied by two penumbra regions 33 produced on two respective outer sides thereof along the array direction Da. That is, as illustrated in FIG. 3, the radiographic apparatus 1 according to the first exemplary embodiment applies main X-ray beams and penumbra beams to the X-ray detecting unit 3 and thus forms a main exposed area having a length Li and penumbra areas on the X-ray detecting unit 3, the penumbra areas being formed on the two respective outer sides of the main exposed area.

As described above, a penumbra is an unnecessary component of X-rays and spreads toward the outer side of the main exposed area, which is necessary for acquiring a radiographic image. Therefore, the penumbra tends to leak to the outside of the radiographic apparatus.

To suppress the leakage of the penumbra to the outside of the radiographic apparatus, the entirety of the radiographic apparatus may be covered with a shielding member. In such a configuration, however, the weight increases and the center of gravity is raised. Consequently, the radiographic apparatus becomes unstable with unbalanced weight distribution, increasing the probability of image blurring during imaging. Alternatively, the shielding member may be extended beyond the outer periphery of the X-ray generating unit toward the outer periphery of the X-ray detecting unit. In such a configuration also, image blurring during imaging tends to occur because of the reduced stability with unbalanced weight distribution of the radiographic apparatus that is attributed to the increase in weight and the raising of the center of gravity.

The above two alternative configurations each have a problem in that the shielding member becomes tall and gives the examinee a sense of oppression near his/her upper body, and reduces the ease of operation to be performed by the radiologist.

The present inventors have quantified the range of the penumbra on the basis of the geometric dimensions of the forward shielding member 10 included in the X-ray generating unit 2 and the distance between the forward shielding member 10 and the detecting portion 15 of the X-ray detecting unit 3. Furthermore, on the basis of the quantified range of the penumbra, the present inventors have found a specific configuration in which the occurrence of any penumbras that may go past the X-ray detecting unit 3 and reach an area below the X-ray detecting unit 3 is effectively reduced with a reduced proportion of the shielding members. The specific configuration found by the present inventors is characterized by the X-ray detecting unit 3 having an improved shape on the outer sides thereof along the array direction Da.

In the specific configuration according to the present invention, the leakage of penumbras can be reduced without reducing the stability in terms of weight distribution of the radiographic apparatus 1, whereby the radiographic apparatus 1 can provide superior imaging performance and usability.

The penumbra regions 33 each have a specific spatial size along the array direction Da that depends on a focal spot diameter PHI as the size of each focal spot 13 along the array direction Da, the height $h_0$ of the partitions 39, and a source-to-image distance $D_{SI}$ as the distance from the targets 8 to the detecting portion 15. If the height $h_0$ of the partitions 39 is set to the same value as the source-to-image distance $D_{SI}$, penumbras can be eliminated theoretically. In such a case, however, the plurality of main exposed regions 38 do not coincide with one another on a detecting plane 41. To allow the plurality of main exposed regions 38 to coincide with one another on the detecting plane 41, the height $h_0$ of the partitions 39 is limited to a predetermined maximum height $h_{max}$ or smaller.

As illustrated in FIG. 2A, the height $h_0$ is defined as the length of the partitions 39 from the electron incident surfaces 7 in the direction of the normal line 44 with respect to the electron incident surfaces 7. The detecting plane 41 contains the detecting portion 15 and is defined as a virtual plane spreading around the detecting portion 15.

Figure 3:
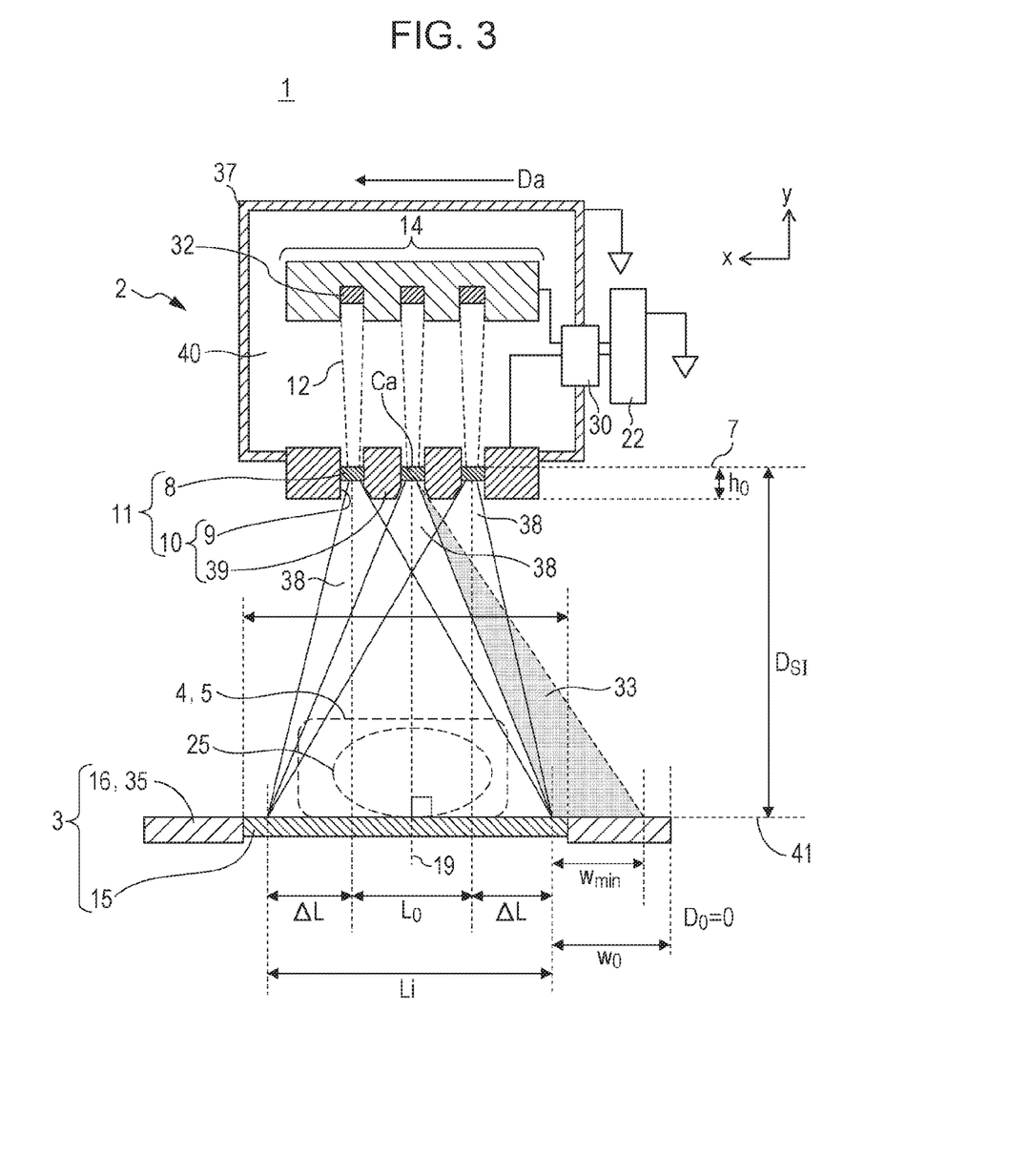
FIG. 3 is a schematic diagram of a radiographic apparatus according to a first exemplary embodiment of the present invention.

If the detecting portion 15 is a flat plane as illustrated in FIG. 3, the detecting plane 41 is defined as a virtual flat plane containing the detecting portion 15. If the detecting portion 15 is parallel to the electron incident surfaces 7 as illustrated in FIG. 3, the detecting plane 41 is uniquely determined as a virtual plane whose normal line corresponds to a perpendicular line 19 extending perpendicularly from the array center Ca, along the array direction Da, of the target array 11 toward the detecting portion 15.

As illustrated in FIG. 3, the shielding portions 16 are provided on the respective outer sides of the detecting portion 15 along the array direction Da and on the respective outer sides of an area having a main exposed length Li by which the main exposed regions 38 coincide with one another. The shielding portions 16 can be made of a material having high X-ray absorptance. The shielding portions 16 may alternatively be made of metal such as stainless steel or aluminum, as long as the shielding portions 16 each have a thickness that can attenuate the X-rays by a required amount. The shielding portions 16 can each be provided as a member containing at least any one of the following metallic elements: lead, gold, platinum, silver, tungsten, molybdenum, tantalum, copper, nickel, iron, titanium, silicon carbide, and aluminum.

In the first exemplary embodiment illustrated in FIG. 3, the shielding portions 16 each include an outer shielding portion 35 that extends on the outer side of the detecting portion 15 along the array direction Da. The shielding portions 16 according to the first exemplary embodiment each have a predetermined width $w_0$. A height $D_0$ of each of the shielding portions 16 with respect to the detecting plane 41 is zero.

In the first exemplary embodiment, the outer shielding portion 35 is provided in an area having the width $w_0$, the area extending toward the outer side along the array direction Da by a length larger than a penumbra length $w_{min}$. The penumbra length $w_{min}$ corresponds to a width of each penumbra region 33 on the detecting plane 41 in a case where the shielding portions 16 are not provided. Therefore, in the first exemplary embodiment, the penumbra regions 33 are produced within an area over which the X-ray detecting unit 3 extends. Hence, the leakage of penumbras to the outside of the radiographic apparatus 1 is reduced.

As described above, in the radiographic apparatus 1 including the plurality of targets 8 and the partitions 39 that separate the targets 8 from one another, the shielding portions 16 are technically significant in effectively reducing the leakage of penumbras to the outside with a reduced proportion of the shielding members.

Now, conditions for the height $D_0$ and the width $w_0$ of the shielding portions 16 that are required for producing the effect of reducing the leakage of penumbras to the outside will be described. The height $D_0$ and the width $w_0$ of the shielding portions 16 and the height $h_0$ of the partitions 39 are defined complementarily to one another as described below.

The first exemplary embodiment includes not only a case where the height $D_0$ is 0 but also a case where the height $D_0$ is larger than 0. The shielding portions 16 each have a predetermined height $D_0$ that is larger than zero (not shown), the height $D_0$ and the width $w_0$ of the shielding portions 16 and the height $h_0$ of the partitions 39 complementarily satisfy Expressions (1) to (3) given below. Details will now be described.

In the first exemplary embodiment, the height $h_0$ of the partitions 39 satisfies Expression (1):

[Math. 1]

$$h_0 \le h_{max} = \frac{p}{p+Li} D_{SI} \quad (1)$$

where p denotes the focal spot pitch, and Li denotes the length by which the main exposed regions 38 coincide with one another on the detecting plane 41. By making the focal spot pitch p sufficiently large relative to the length Li, the main exposed regions 38 can be made to coincide with one another on the detecting plane 41 even if the height $h_0$ of the partitions 39 is as large as the source-to-image distance $D_{SI}$. However, increasing the focal spot pitch p means limiting the resolution in the depth direction in the tomography. Therefore, the focal spot pitch p is preferably a small value relative to the length Li, more preferably, smaller than 1/10 of the length Li. Hence, the height $h_0$ is limited to a value that is sufficiently smaller than the source-to-image distance $D_{SI}$. Letting the main exposed length, which is the length of the main exposed area, be Lm, the length Li by which the main exposed regions 38 coincide with one another satisfies a relationship of Li≤Lm.

Letting the length of the array of the targets 8 be $L_0$ and the length of each of portions of the main exposed area that spread toward the respective outer sides beyond the area defined by the length $L_0$ be DELTA-L, the main exposed length Lm is expressed as Lm=$L_0$+2×DELTA-L. Note that the array length $L_0$ is uniquely defined as the distance between the centers of two focal spots 13 formed by two targets 8 that are at the extreme ends, respectively, of the target array 11.

Letting the diameter of the focal spots 13, the number of targets 8 included in the target array 11, and the diameter of the apertures 9 provided in the forward shielding member 10 be PHI, n, and PSI, respectively, $L_0$=(n−1)×p and DELTA-L=1/2×{PHI+($D_{SI}/h_0$)×(PSI−PHI)} hold.

Hence, the main exposed length Lm along the array direction Da is expressed by (n−1)×p+{PHI+($D_{SI}/h_0$)×(PSI−PHI)}.

Here, the focal spot diameter PHI is a diameter of each of the focal spots 13 along the array direction Da, the number n is the number of targets 8 included in the target array 11, and the aperture diameter PSI is the length, along the array direction Da, of each of the apertures 9 provided in the forward shielding member 10.

Expression (1) means that the height $h_0$ of the partitions 39 included in the forward shielding member 10 is smaller than or equal to the maximum height $h_{max}$ given on the right side of the sign of inequality in Expression (1). If the height $h_0$ of the partitions 39 included in the forward shielding member 10 satisfies Expression (1), the X-ray generating unit 2 can make the main exposed regions 38 coincide with one another by the length Li on the detecting plane 41 of the X-ray detecting unit 3.

To allow the X-ray beams corresponding to the main exposed regions 38 to be applied to the object 25 from different angles, the partitions 39 each include at least a member that shields the examinee or the operator from X-rays. Specifically, the partitions 39 each contain at least any one of the following metallic elements: lead, gold, platinum, silver, tungsten, molybdenum, tantalum, copper, nickel, and iron.

Now, conditions for the width $w_0$ and the height $D_0$ of the shielding portions 16 will be described specifically. The width $w_0$ and the height $D_0$ of the shielding portions 16 satisfy Expressions (2) and (3), respectively:

[Math. 2]

$$w_0 \ge w_{min} = \frac{D_{SI} - h_0}{h_0} \Phi \quad (2)$$

[Math. 3]

$$D_0 < 2\Phi \cdot D_{SI} \cdot \left(\frac{D_{SI} - h_0}{2D_{SI}\Phi + h_0(\Psi - \Phi)}\right) \cdot \left(1 - \frac{w_0}{\Phi} \times \frac{h_0}{D_{SI} - h_0}\right) \quad (3)$$

Expression (3) represents a condition that the effect of reducing the leakage of penumbras cannot be produced only by defining the height $D_0$ of the shielding portions 16. Under the condition represented by Expression (3), if the width $w_0$ is larger than or equal to the minimum width (penumbra length) $w_{min}$ given on the right side of the sign of inequality in Expression (2), the leakage of penumbras can be reduced by the shielding portions 16 that include the respective outer shielding portions 35 as illustrated in FIG. 3.

The penumbra length $w_{min}$ is the length of an area to which the penumbra regions 33 are applied to the detecting plane 41 in the case where the height $D_0$ of the shielding portions 16 is zero. The penumbra length $w_{min}$ corresponds to the length of an area that extends toward the outer side along the array direction Da by a length expressed as $\{(D_{SI}-h_0)/h_0\times\}\times$PHI from the edge of the main exposed area.

Second Exemplary Embodiment

A second exemplary embodiment illustrated in FIG. 4 will now be described, focusing on a relationship to be satisfied among the height $h_0$ of the partitions 39 and the width $w_0$ and the height $D_0$ of the shielding portions 16. The second exemplary embodiment differs from the first exemplary embodiment in that the shielding portions 16 includes the outer shielding portions 35 and upright shielding portions 36. The outer shielding portions 35 extend on the outer sides, respectively, of the detecting portion 15 along the array direction Da. The upright shielding portions 36 extend from the detecting plane 41 toward the target array 11. In the second exemplary embodiment, the shielding portions 16 have a predetermined height $D_0$ and a predetermined width $w_0$.

In the second exemplary embodiment also, the height $h_0$ of the partitions 39 needs to satisfy the condition that the main exposed regions 38 coincide with one another on the detecting plane 41 while forming a main exposed area having the length Lm containing the predetermined length Li. Hence, the height $h_0$ of the partitions 39 needs to satisfy Expression (1) given in the first exemplary embodiment.

Figure 4:
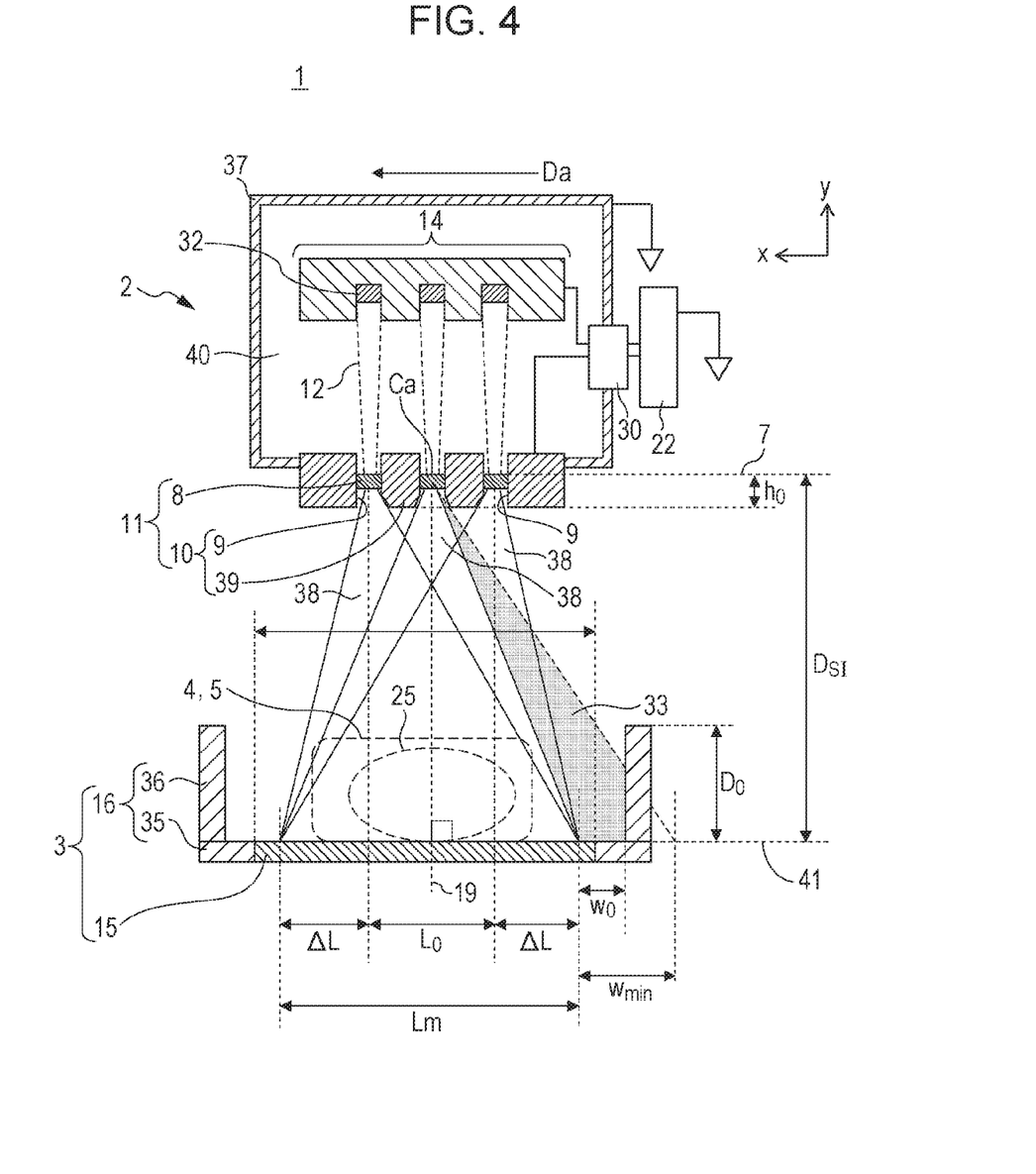
FIG. 4 is a schematic diagram of a radiographic apparatus according to a second exemplary embodiment of the present invention.

In the second exemplary embodiment illustrated in FIG. 4, the shielding portions 16 have a width that is smaller than the minimum width (penumbra length) $w_{min}$ defined by the right side of Expression (2). The width $w_0$ and the height $D_0$ of the shielding portions 16 included in the X-ray detecting unit 3 according to the second exemplary embodiment satisfy Expressions (4) and (5), respectively:

[Math. 4]
$$w_0 < w_{min} = \frac{D_{SI} - h_0}{h_0}\Phi \qquad (4)$$

[Math. 5]
$$D_0 \geq 2\Phi \cdot D_{SI} \cdot \left(\frac{D_{SI} - h_0}{2D_{SI}\Phi + h_0(\Psi - \Phi)}\right) \cdot \left(1 - \frac{w_0}{\Phi} \times \frac{h_0}{D_{SI} - h_0}\right) \qquad (5)$$

Expression (4) represents a condition that the effect of reducing the leakage of penumbras cannot be produced only by defining the width $w_0$ of the shielding portions 16. Under the condition represented by Expression (4), if the height $D_0$ of the shielding portions 16 is larger than or equal to the minimum value given on the right side of Expression (5), the leakage of penumbras can be reduced by the shielding portions 16 that include the outer shielding portions 35 and the upright shielding portions 36 as illustrated in FIG. 4. Hence, in the second exemplary embodiment also, the width $w_0$ and the height $D_0$ of the shielding portion 16 and the height $h_0$ of the partitions 39 are defined complementarily to one another, as in the first exemplary embodiment.

As described above, in the first or second exemplary embodiment, the shielding portions 16 each include at least a part extending in the penumbra region 33 and a part overlapping the penumbra area on the detecting plane 41; or the shielding portions 16 each include a part extending on the outer side of the penumbra region 33 along the array direction Da and a part extending along the detecting plane 41 and on the outer side of the penumbra area. Extending on the outer side along the array direction Da means extending over an area that is farther than the penumbra area from the perpendicular line 19 extending from the array center Ca of the target array 11 toward the detecting portion 15.

The present invention also encompasses an embodiment in which the X-ray detecting unit 3 includes the shielding portion 16 according to the first exemplary embodiment on one of the two outer sides along the array direction Da and the shielding portion 16 according to the second exemplary embodiment on the other outer side along the array direction Da.

The length Li by which the plurality of main exposed regions 38 coincide with one another on the detecting plane 41 can be identified by sequentially applying the electron beams 12 to the respective targets 8 and measuring the main exposed length Lm along the array direction Da for each of the electron beams 12. The main exposed area and the penumbra area can be identified by providing a pinhole mask between the targets 8 and the X-ray detecting unit 3 and measuring the focal images.

As described in each of the first and second exemplary embodiments, the shielding portions 16 can be provided in various other ways, as long as the shielding portions 16 are provided in areas where the leakage of penumbras is reduced. FIGS. 5A to 5D illustrate different modifications concerning the arrangement of each of the shielding portions 16 and the detecting portion 15.

Figure 5A:
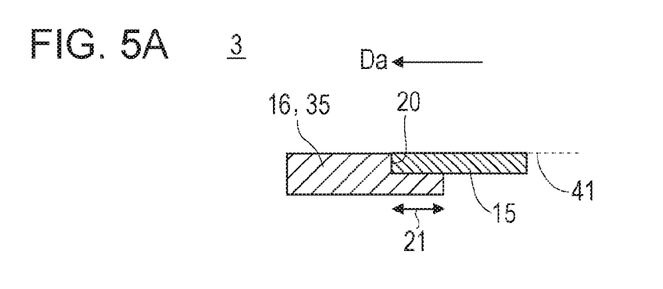
FIGS. 5A to 5D are schematic diagrams illustrating modifications of the X-ray detecting unit included in the radiographic apparatus according to the general embodiment of the present invention.

FIG. 5A illustrates a first modification in which the shielding portion 16 including the outer shielding portion 35 is connected to the detecting portion 15. The first modification differs from the first exemplary embodiment illustrated in FIG. 3 in that the shielding portion 16 includes a part 21 overlapping the detecting portion 15 on a side of the detecting portion 15 that is opposite the detecting plane 41.

Figure 5B:
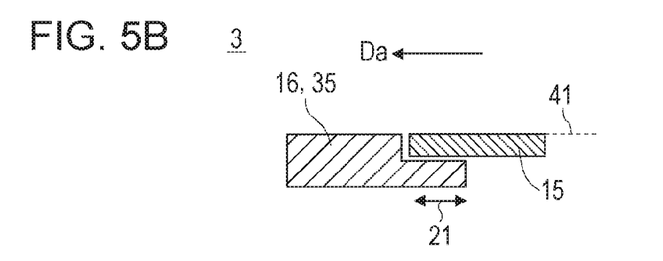

FIG. 5B illustrates a variation of the first modification illustrated in FIG. 5A. The variation differs from the first modification illustrated in FIG. 5A in that a gap is interposed between the shielding portion 16 and the detecting portion 15. In such a case where the shielding portion 16 and the detecting portion 15 are not continuous with each other as in this variation, if the gap has a specific size along the array direction Da, the effect of reducing the leakage of penumbras to an area below the X-ray detecting unit 3 is produced.

Figure 5C:
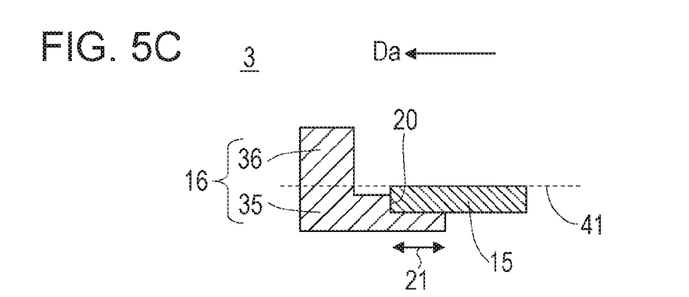

FIG. 5C illustrates a second modification in which the shielding portion 16 including the outer shielding portion 35 and the upright shielding portion 36 is connected to the detecting portion 15. The second modification differs from the second exemplary embodiment illustrated in FIG. 4 in that the outer shielding portion 35 includes a part 21 that overlap the detecting portion 15 on a side of the detecting portion 15 that is opposite the detecting plane 41.

Figure 5D:
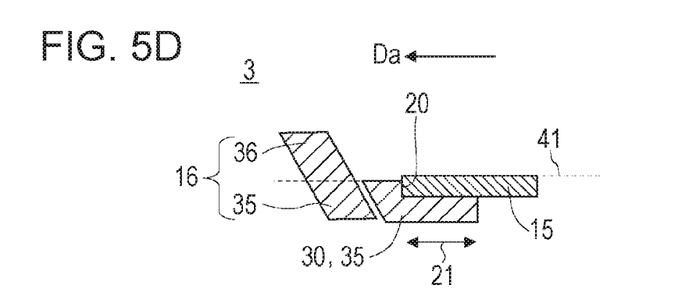

FIG. 5D illustrates a variation of the second modification illustrated in FIG. 5C. The variation differs from the second modification illustrated in FIG. 5C in that the shielding portion 16 includes a plurality of members that are arranged with a gap interposed therebetween, and in that the upright shielding portion 36 is inclined with respect to the detecting plane 41.

In each of the first and second modifications illustrated in FIGS. 5A and 5C, the shielding portion 16 includes a part 20 that is in contact with the outer edge of the detecting portion 15 and a part that extends from the part 20 that is in contact with the outer edge of the detecting portion 15 toward the outer side along the array direction Da. In each of the cases illustrated in FIGS. 5A to 5D, the shielding portion 16 includes the part 21 overlapping the detecting portion 15 and the part extending from the part 21 toward the outer side along the array direction Da.

The present invention encompasses an embodiment in which a pair of shielding portions 16 are provided on two respective outer sides of the detecting portion 15 along the array direction Da, as illustrated in FIG. 3 or 4.

The height $h_0$ of the partitions 39 satisfies Expression (6) given below. Thus, the width of each penumbra region 33 along the array direction Da is reduced, leading to a size reduction of the radiographic apparatus 1.

[Math. 6]

$$h_0 \geq \frac{1}{10} \frac{p}{p+Li} D_{Sl} \quad (6)$$

From the viewpoint of the size reduction of the radiographic apparatus 1, the height $h_0$ of the partitions 39 is more preferably within a range from 2 mm or larger to 20 mm or smaller.

The shielding portions 16 only need to be included in the X-ray detecting unit 3 in such a manner as to be positioned in the respective penumbra regions 33. As illustrated in FIG. 3, the outer end of each of the shielding portions 16 along the array direction Da may extend by the width $w_0$, i.e., up to a position on the outer side of a corresponding one of the penumbra regions 33. In the first or second embodiment illustrated in FIG. 3 or 4, the inner end of each of the shielding portions 16 along the array direction Da is positioned on the outer side of an area defined by the length Li corresponding to the main exposed length Lm. Alternatively, the inner end of the shielding portion 16 along the array direction Da may overlap an end portion of the area defined by the length Li, or may be positioned on the inner side of the area defined by the length Li.

If the inner end of the shielding portion 16 is positioned on the inner side of the area defined by the length Li, the inner end of the shielding portion 16 is desirably positioned in an area that does not overlap a site of interest of the object 25. Compared with a configuration (not illustrated) in which penumbras are shielded by the detecting portion 15 and the shielding portions 16, the configuration according to any of the above exemplary embodiments in which penumbras are shielded only by the shielding portion 16 allows high-cost X-ray detecting devices to be provided at a higher density in the area defined by the length Li by which the main exposed regions 38 coincide with one another. Consequently, according to any of the above exemplary embodiments, the radiographic apparatus 1 can be provided with a higher imaging resolution but at a lower cost.

Figure 6:
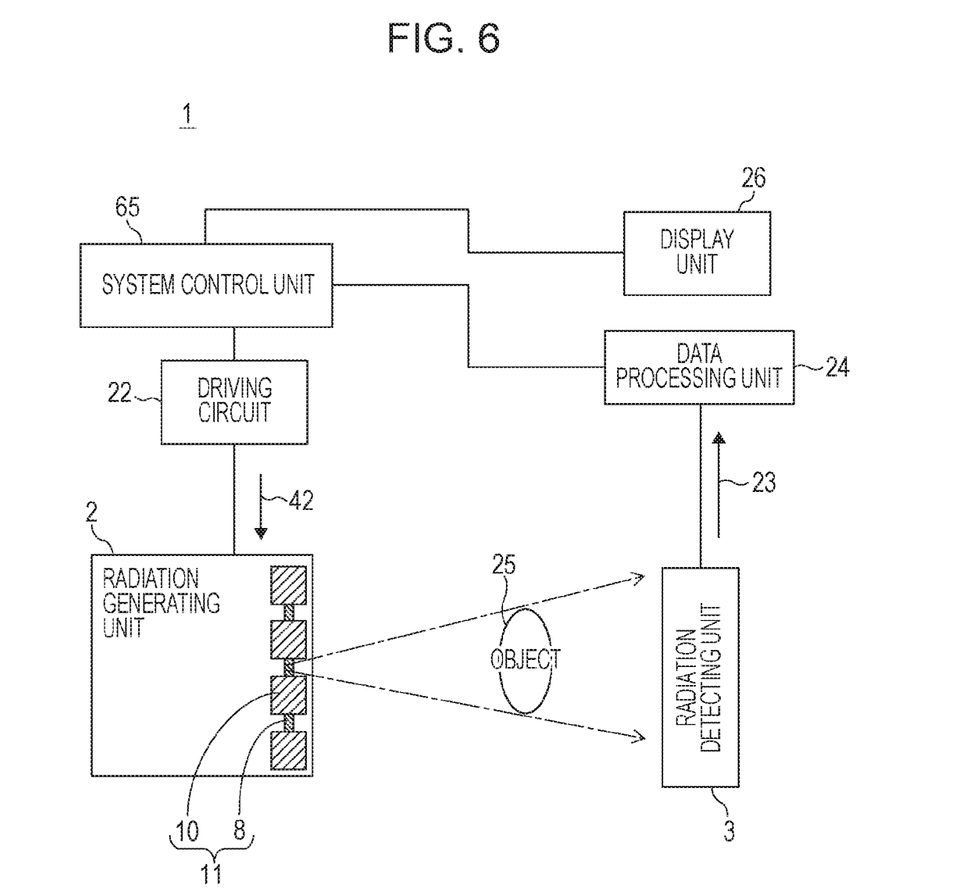
FIG. 6 is a system diagram of the radiographic apparatus according to the general embodiment of the present invention.

An exemplary system configuration of the radiographic apparatus 1 according to the general embodiment of the present invention will now be described with reference to FIG. 6.

The X-ray generating unit 2 and the X-ray detecting unit 3 are controlled in conjunction with each other by a system control unit 65. The driving circuit 22, which is controlled by the system control unit 65, outputs a control signal 42 to the X-ray generating unit 2. In accordance with the control signal 42, the state of emission of the X-ray beams emitted from the X-ray generating unit 2 is controlled. The X-ray beams emitted from the X-ray generating unit 2 are transmitted through the object 25 and are detected by the X-ray detecting unit 3. The X-ray detecting unit 3 converts the detected X-ray beams into a radiographic image 23 and outputs the radiographic image 23 to a data processing unit 24. The data processing unit 24, which is controlled by the system control unit 65, performs a predetermined signal processing operation on the radiographic image 23 and outputs the radiographic image 23 thus processed to the system control unit 65. In receipt of the radiographic image 23 that has been subjected to signal processing, the system control unit 65 outputs to the display unit 26 a display signal for displaying an image on a display unit 26. The display unit 26 displays an image that is based on the display signal on a screen as an image of the object 25.

Now, tomosynthesis imaging performed by using the radiographic apparatus 1 according to the general embodiment will now be described with reference to FIG. 6. In tomosynthesis imaging, X-ray beams are sequentially applied to the object 25 from the plurality of targets 8. The X-ray beams that have been transmitted through the object 25 are detected by the X-ray detecting unit 3, whereby a plurality of images are taken. The plurality of images thus taken are reconstructed by the data processing unit 24, whereby a tomographic image is formed.

In the first or second exemplary embodiment illustrated in FIG. 3 or 4, the object positioning portion 4 can function as a breast inserting portion 5 into which a breast of the examinee is to be inserted in a direction intersecting both the array direction Da and the perpendicular line 19. In such a configuration, the radiographic apparatus 1 according to the general embodiment of the present invention is used for mammotomography in which a plurality of images are acquired at different angles about the direction in which the mammary glands extend.

In the case where the radiographic apparatus 1 according to the general embodiment of the present invention is applied to mammotomography, the general embodiment encompasses a modification in which a pressing plate (not illustrated) is provided between the object positioning portion 4 and the forward shielding member 10. The pressing plate presses the breast by reducing the distance to the detecting portion 15, whereby the detection of any abnormal portions such as calcified portions that tend to overlap mammary glands in the thickness direction of the breast is facilitated.

Hence, according to the general embodiment of the present invention, there is provided a radiographic apparatus that has a satisfactory main exposed length Li, a satisfactory resolution in the depth direction, and reduces the leakage of penumbras toward the outer side along the array direction Da. With such a radiographic apparatus according to the general embodiment of the present invention, the amount of unnecessary exposure of the radiologist and the examinee to leaked X-rays is reduced, and tomography with a high resolution in the depth direction can be implemented.

Now, a third exemplary embodiment and a fourth exemplary embodiment of the present invention will be described with reference to FIGS. 7 to 9.

The third and fourth exemplary embodiments concern a case where the radiographic apparatus 1 according to the general embodiment of the present invention is applied to mammotomography, and are intended to reduce unnecessary X-ray exposure of the body of the examinee. The third and fourth exemplary embodiments are characterized in the shapes of the X-ray generating unit 2 and the forward shielding member 10.

Figure 7:
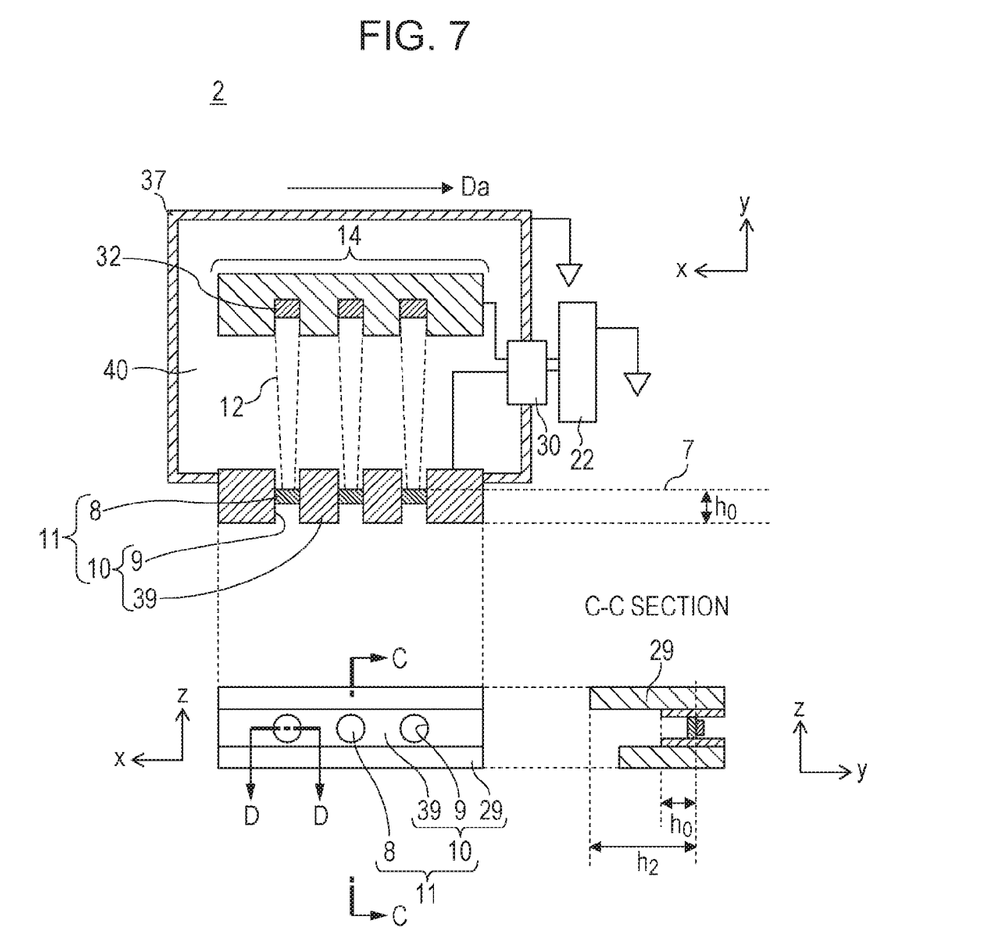
FIG. 7 is a three-way view of an X-ray generating unit included in a radiographic apparatus according to a third or fourth exemplary embodiment of the present invention.

FIG. 7 is a three-way view of an X-ray generating unit 2 included in a radiographic apparatus 1 according to the third or fourth exemplary embodiment. In the third or fourth exemplary embodiment, the forward shielding member 10 extends along the array direction Da and includes a pair of shielding walls 29 that hold the partitions 39 therebetween. At least one of the shielding walls 29 has a height $h_2$ that is larger than the height $h_0$ of the partitions 39 ($h_2 > h_0$). The height $h_2$ is defined as the length from the electron incident surfaces 7 of the targets 8 in the direction of the line normal to the electron incident surfaces 7 toward the X-ray detecting unit 3, as with the height $h_0$.

Third Exemplary Embodiment

Figure 8:
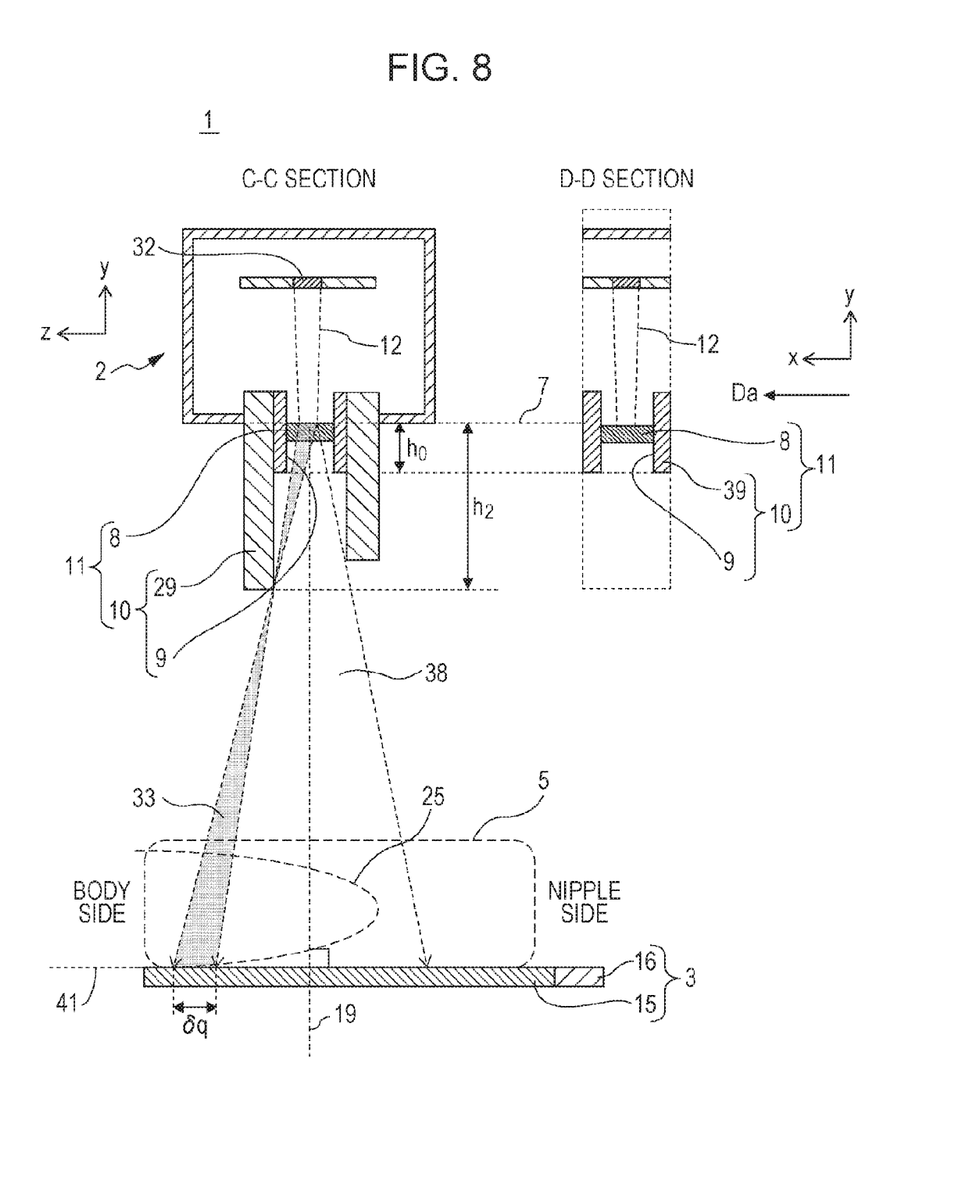
FIG. 8 is a schematic diagram of a radiographic apparatus according to the third exemplary embodiment of the present invention.

As illustrated in FIG. 8, in the radiographic apparatus 1 according to the third exemplary embodiment, one of the shielding walls 29 that has the height $h_2$ is provided on a side nearer to the body of the examinee than the apertures 9 in a direction intersecting the array direction Da. In the configuration according to the third exemplary embodiment, unnecessary X-ray exposure of the body of the examinee is reduced. Unnecessary X-rays include penumbras that are attributed to the size of the focal spots, the height of the forward shielding member 10, and the source-to-image distance. In the third exemplary embodiment, the penumbras to be considered as the problem occur on the respective outer sides in the direction intersecting the array direction Da. In particular, a component that leaks toward the body of the examinee is the problem.

Letting the length of the penumbra on the detecting plane 41 in a direction perpendicular to the array direction Da be δq, if the height $h_2$ satisfies Expression (7) below, the leakage of the penumbra occurring on the outer side in the direction intersecting the array direction Da is effectively reduced.

[Math. 7]

$$h_2 \geq \frac{D_{SI} \cdot \Phi}{\delta q + \Phi} \quad (7)$$

While FIGS. 7 and 8 each illustrate a case where a pair of shielding walls 29 are provided, the present invention also encompasses an embodiment in which only one of the shielding walls 29 that has the height $h_2$ ($>h_0$) is provided. In such an embodiment, the shielding wall 29 is provided on the side nearer to the body of the examinee than the apertures 9.

With the radiographic apparatus 1 according to the third exemplary embodiment, mammotomography is implemented with smaller penumbras leaking toward the outer sides along the array direction Da and with a smaller penumbra leaking in the direction intersecting the array direction Da and toward the body of the examiner.

Fourth Exemplary Embodiment

Figure 9:
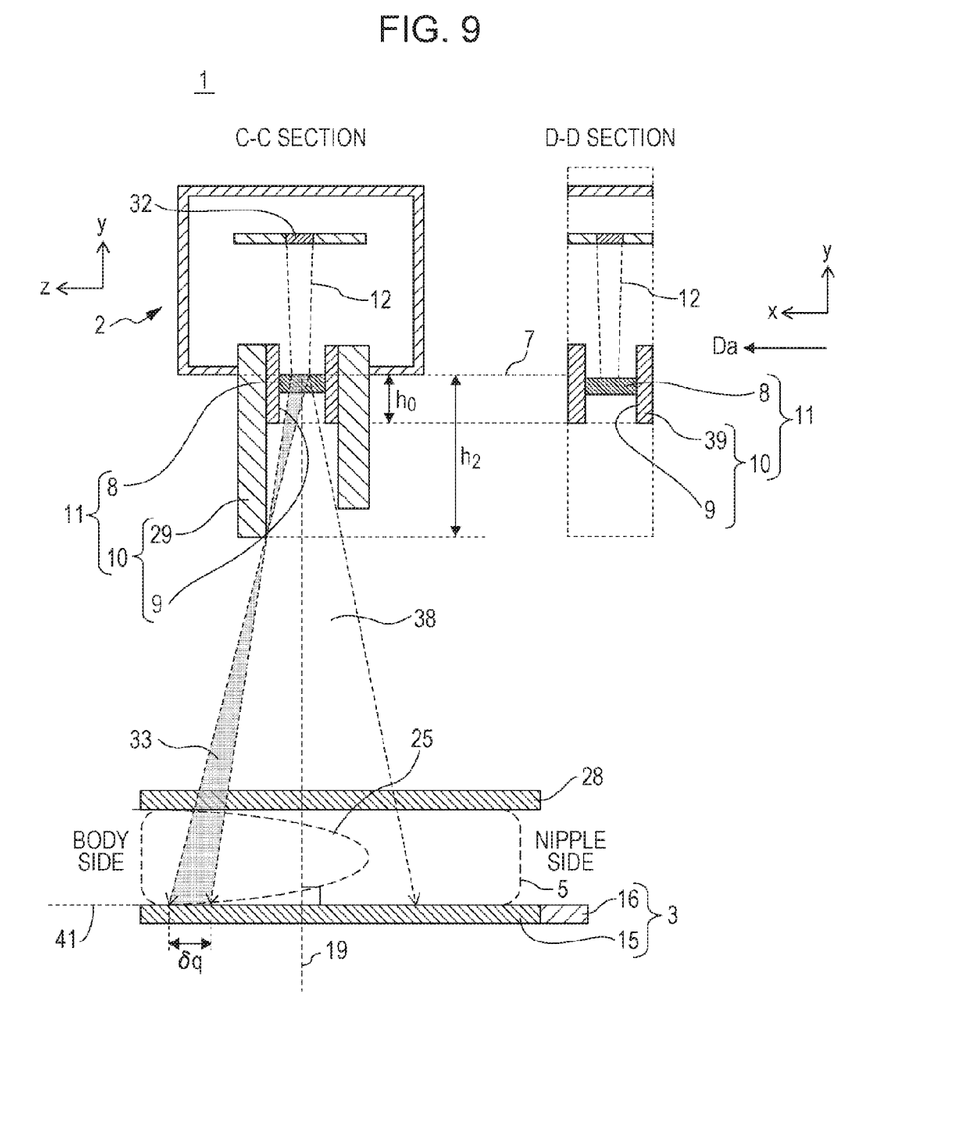
FIG. 9 is a schematic diagram of a radiographic apparatus according to the fourth exemplary embodiment of the present invention.

The fourth exemplary embodiment illustrated in FIG. 9 is a modification of the third exemplary embodiment and differs from the third exemplary embodiment in including a pressing plate 28 provided between the breast inserting portion 5 and the forward shielding member 10.

In the radiographic apparatus 1 according to the fourth exemplary embodiment, the breast is pressed by bringing the pressing plate 28 close to the detecting portion 15. Such a configuration improves the performance in detecting any abnormal portions such as calcified portions that tend to be overlooked when overlapping normal portions such as mammary glands in the direction of the perpendicular line 19.

Advantageous Effects of Invention

In the radiographic apparatus according to any of the above embodiments of the present invention including the plurality of targets and the forward shielding member that has the apertures provided in correspondence with the targets, penumbras that may go past the X-ray detecting unit can be reduced effectively without reducing the stability in terms of the weight distribution of the apparatus.

With the X-ray generating unit according to any of the embodiments of the present invention, image blurring that may occur in the known X-ray source because of the rotational movement of the X-ray source is avoided, and scattering of X-rays that may be caused by the forward shielding member is reduced. Thus, radiography that is superior in imaging performance and usability is implemented.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-247133, filed Nov. 29, 2013, which is hereby incorporated by reference herein in its entirety.

The invention claimed is:

1. A radiographic apparatus comprising:
an X-ray generating unit that includes
  a target array including a plurality of targets that are arrayed in a line and a forward shielding member, the forward shielding member including a plurality of partitions each having a height configured to separate adjacent ones of the targets, and
  an electron emitting source that emits electron beams to electron incident surfaces of the plurality of targets, respectively, and forms a focal spot on each one of the plurality of targets; and
an X-ray detecting unit that includes
  a detecting portion facing the target array and including a plurality of detecting devices, and
  a shielding portion provided on an outer side of the detecting portion along an array direction in which the targets are arrayed in a line,
wherein the target array of the X-ray generating unit is distant from the detecting portion via a gap having a source-to-image distance and forms a pair of penumbra areas and a main exposed area between the pair of penumbra areas on the X-ray detecting unit,
wherein a size of the pair of penumbra areas being formed depends on a focal spot diameter, the height of the partitions and the source-to-image distance between the targets and the detecting portion, and
wherein the shielding portion includes a part that is positioned on the outer side of the penumbra areas along the array direction.

2. The radiographic apparatus according to claim 1, wherein the shielding portion includes at least a contact part provided in contact with an outer edge of the detecting portion and a part extending from the contact part toward the outer side along the array direction, or an overlapping part overlapping the detecting portion along the array direction and a part extending from the overlapping part toward the outer side along the array direction.

3. The radiographic apparatus according to claim 1, wherein the shielding portion is provided on each of two outer sides of the detecting portion along the array direction.

4. The radiographic apparatus according to claim 1, wherein the main exposed area is defined by a main exposed length Lm along the array direction, the main exposed length Lm being expressed as (n−1)×p+{PHI+ ($D_{SI}$/$h_0$)×(PSI−PHI)}, where $h_0$ denotes the height of each of the partitions extending toward a side across the electron incident surfaces from the electron emitting source; PHI denotes the focal spot diameter of each of focal spots formed on the respective electron incident surfaces by the electron emitting source; p denotes a focal spot pitch; n denotes a number of targets that are arrayed; PSI denotes an aperture diameter determined by adjacent ones of the partitions; and $D_{SI}$ denotes the source-to-image distance by which the detecting portion is distant from the electron incident surfaces.

5. The radiographic apparatus according to claim 4, wherein the penumbra areas extend from an edge of the main exposed area along the array direction and toward the outer side along the array direction by a penumbra length $w_{min}$ expressed as {($D_{SI}$−$h_0$)/$h_0$}×PHI.

6. The radiographic apparatus according to claim 4, wherein the height $h_0$ of the partitions, a width $w_0$ of the shielding portion, and a height $D_0$ of the shielding portion satisfy at least Expressions (1), (2), and (3), respectively, or Expressions (1), (4), and (5), respectively:

[Math. 1]
$$h_0 \leq h_{max} = \frac{p}{p+Li}D_{SI} \quad (1)$$

[Math. 2]
$$w_0 \geq w_{min} = \frac{D_{SI}-h_0}{h_0}\Phi \quad (2)$$

[Math. 3]
$$D_0 < 2\Phi \cdot D_{SI} \cdot \left(\frac{D_{SI}-h_0}{2D_{SI}\Phi + h_0(\Psi-\Phi)}\right) \cdot \left(1 - \frac{w_0}{\Phi} \times \frac{h_0}{D_{SI}-h_0}\right) \quad (3)$$

[Math. 4]
$$w_0 < w_{min} = \frac{D_{SI}-h_0}{h_0}\Phi \quad (4)$$

[Math. 5]
$$D_0 \geq 2\Phi \cdot D_{SI} \cdot \left(\frac{D_{SI}-h_0}{2D_{SI}\Phi + h_0(\Psi-\Phi)}\right) \cdot \left(1 - \frac{w_0}{\Phi} \times \frac{h_0}{D_{SI}-h_0}\right) \quad (5)$$

where Li denotes a length by which X-ray beams emitted from the respective targets coincide with one another on a detecting plane and form the main exposure area.

7. The radiographic apparatus according to claim 6, wherein the height $h_0$ satisfies Expression (6):

[Math. 6]
$$h_0 \geq \frac{1}{10}\frac{p}{p+Li}D_{SI}. \quad (6)$$

8. The radiographic apparatus according to claim 4, wherein the height $h_0$ is 2 mm or larger and 20 mm or smaller.

9. The radiographic apparatus according to claim 1, wherein the partitions each contain at least any one of metallic elements, which are lead, gold, platinum, silver, tungsten, molybdenum, tantalum, copper, nickel, and iron.

10. The radiographic apparatus according to claim 1, wherein the shielding portion contains at least any one of metallic elements, which are lead, gold, platinum, silver, tungsten, molybdenum, tantalum, copper, nickel, iron, titanium, silicon carbide, and aluminum.

11. The radiographic apparatus according to claim 1, further comprising:
a driving circuit connected to the X-ray generating unit and that drives the X-ray generating unit;
a data processing unit connected to the X-ray detecting unit and that acquires a radiographic image outputted from the X-ray detecting unit; and
a control unit that controls, via the driving circuit and the data processing unit, the X-ray generating unit and the X-ray detecting unit, respectively, that are in conjunction with each other.

12. The radiographic apparatus according to claim 1, further comprising:
an object positioning portion provided between the detecting portion and the target array,
wherein the object positioning portion functions as a breast inserting portion into which a breast of an examinee is to be inserted in a direction intersecting both the array direction and a line perpendicular to each of the electron incident surfaces.

13. The radiographic apparatus according to claim 12, wherein the X-ray generating unit includes a shielding wall extending along the array direction and provided on a side nearer to a body of the examinee than the partitions, the shielding wall having a height $h_2$ that is larger than the height $h_0$ of the partitions.

14. The radiographic apparatus according to claim 13, wherein the height $h_2$ satisfies Expression (7):

[Math. 7]
$$h_2 \geq \frac{D_{SI} \cdot \Phi}{\delta q + \Phi} \quad (7)$$

where δq denotes a length of the penumbra area in a direction perpendicular to the array direction.

15. The radiographic apparatus according to claim 12, further comprising a pressing plate provided between the breast inserting portion and the forward shielding member and that presses the breast by reducing a distance to the detecting portion.

16. The radiographic apparatus according to claim 1, wherein the shielding portion does not include an X-ray detecting element.

* * * * *